United States Patent
Takano et al.

(10) Patent No.: US 9,021,866 B2
(45) Date of Patent: May 5, 2015

(54) GAS LEAK DETECTOR

(71) Applicants: Yoshihiko Takano, Iruma (JP); Xiao-Jing Zhou, Iruma (JP); Noriyoshi Yokosuka, Iruma (JP)

(72) Inventors: Yoshihiko Takano, Iruma (JP); Xiao-Jing Zhou, Iruma (JP); Noriyoshi Yokosuka, Iruma (JP)

(73) Assignee: GL Sciences Incorporated, Tokyo (JP)

( * ) Notice: Subject to any disclaimer, the term of this patent is extended or adjusted under 35 U.S.C. 154(b) by 395 days.

(21) Appl. No.: 13/648,539

(22) Filed: Oct. 10, 2012

(65) Prior Publication Data

US 2013/0276517 A1 Oct. 24, 2013

(30) Foreign Application Priority Data

Oct. 11, 2011 (JP) ................. 2011-224123

(51) Int. Cl.
*G01M 3/18* (2006.01)
*G01N 33/00* (2006.01)
*G01M 3/16* (2006.01)

(52) U.S. Cl.
CPC ............. *G01M 3/18* (2013.01); *G01N 33/0022* (2013.01); *G01M 3/16* (2013.01)

(58) Field of Classification Search
CPC G01N 27/18; G01N 33/0022; G01N 33/0026
USPC .............................................. 73/40.5 R, 40.7
See application file for complete search history.

(56) References Cited

U.S. PATENT DOCUMENTS

2004/0051043 A1* 3/2004 Kilian et al. .................. 250/343

FOREIGN PATENT DOCUMENTS

| JP | 03-060060 | 6/1991 |
|---|---|---|
| JP | 09-292302 | 11/1997 |
| JP | 2000-258376 | 9/2000 |
| JP | 2005-307858 | 11/2005 |
| JP | 3127573 | 11/2006 |
| JP | 2009-097393 | 5/2009 |

* cited by examiner

*Primary Examiner* — Paul West
(74) *Attorney, Agent, or Firm* — Jordan and Hamburg LLP

(57) ABSTRACT

A gas-leak detector includes a suction pump that sucks sample gas and reference gas, two gas detection sensors, and a cell block having a cell therein. The cell receives the gasses and has two suction-gas introduction channels and a single gas discharge channel opening thereinto. The gas-leak detector detects a gas leak on the basis of outputs from the sensors. The introduction channels and the discharge channel open into the cell at a first one of opposing surfaces of the cell, the opening of the discharge channel being arranged between the openings of the two introduction channels. The sensors are on the same plane as a second one of the opposing surfaces and are arranged between the opening of the discharge channel and the openings of the introduction channels. The suction pump is arranged on the cell block and communicates with the opening of the discharge channel.

14 Claims, 7 Drawing Sheets

GAS LEAK DETECTOR

CROSS REFERENCES TO RELATED APPLICATIONS

The present invention contains subject matter related to Japanese Patent Application No. 2011-224123 filed in the Japan Patent Office on Oct. 11, 2011, the entire contents of which are incorporated herein by reference.

BACKGROUND OF THE INVENTION

1. Field of the Invention

The present invention relates to a gas-leak detector which is suitable for use as, for example, a gas-leak detector for detecting a leakage of carrier gas of a gas chromatograph (hereinafter abbreviated as GC); which includes a suction pump and gas detection sensors that are small and integrated together to reduce the size and weight of the gas-leak detector and facilitate operation of the gas-leak detector; which has a cell for receiving sucked gasses that has a small capacity so that the gas detection sensors accurately and quickly respond to the gasses and the gas-leak detection sensitivity can be increased; in which pulsation of the suction pump is reduced so that stable detection operation can be achieved; and which can be manufactured at a low cost.

2. Description of the Related Art

In general, a GC includes a sample introduction unit and a separation column that are connected to a pipeline of carrier gas, such as helium gas. The sample introduction unit introduces a sample into a flow of the carrier gas, which carries the sample to the separation column. Components of the sample are separated by the separation column, and the separated components are detected by a detector.

A leakage of the carrier gas from a flow channel that extends from the supply pipeline of the carrier gas to the detector adversely affects the analytical accuracy. If air enters the flow channel at the location of the leakage, the separation column deteriorates at an accelerated pace. Therefore, it is necessary to regularly perform carrier gas leak tests. Gas-leak detectors are used for these tests.

Japanese Unexamined Patent Application Publication No. 9-292302 and Japanese Utility Model Registration No. 3127573, for example, describe examples of gas-leak detectors which include inlets for a probe gas, which is a sample gas, and a reference gas; pipelines that communicate with the inlets; a pump that sucks the gasses; and thermal-conductivity-type gas sensors that detect the gasses. Each gas sensor includes platinum coils connected to a bridge circuit. In gas leak detection, the reference gas, such as air, and the probe gas are sucked and the sensors respond to the sucked gasses. The bridge circuit electrically detects a change in the electric resistances of the sensors, the change corresponding to a change in the temperatures of the sensors caused by a difference between the thermal conductivities of the gasses.

However, since the above-described gas-leak detectors include platinum coils as sensor elements, cells that house the coils have a large capacity, and a large and heavy cell block is used. In addition, since the pump is large and has a large suction capacity, there is a limit to the extent to which the detection sensitivity can be increased, and it is difficult to stabilize the detection operation because of large pulsation and noise. Furthermore, the gas-leak detectors are large and heavy since the pump and the cells that house the sensors are separately arranged.

These problems may be solved by reducing the size of each sensor. Japanese Unexamined Patent Application Publication No. 2000-258376, for example, proposes a chip sensor including a microheater manufactured by silicon micromachining technology so that the microheater is capable of heating a small area of about several tens of micrometers square. The chip sensor may be used as a gas sensor.

Another way to solve the above-described problems is to reduce the size and suction capacity of the pump and stabilize the operation of the pump. This may be achieved by a gas-leak detector that sucks the sample gas and the reference gas through a pumping operation of a diaphragm that is vibrated by a direct-current motor.

However, the pump is still large and has a large suction capacity. Therefore, there is still a limit to the extent to which the detection sensitivity can be increased and it is difficult to stabilize the detection operation because of large pulsation and noise. In addition, the gas-leak detector is large and heavy since the pump and the cells are separately arranged and require individual installation spaces. Furthermore, tailing occurs at the beginning and end of the detection operation, and the detection time and the waiting time required are long when the detection is repeated.

Japanese Unexamined Patent Application Publication Nos. 2009-97393 and 2005-307858, for example, respectively describe a small piezoelectric microblower and a small piezoelectric diaphragm pump that solve the above-described problems of the pump. According to these publications, a piezoelectric element is disposed on one side of a diaphragm, and is connected to a drive device, such as an oscillation circuit. The drive device is operated so as to apply a pulse voltage having a constant frequency to the piezoelectric element and cause the diaphragm to resonate. A blower chamber capable of performing a pumping operation is provided between the diaphragm and a partition plate. The blower chamber communicates with two flow channels that allow fluid to be supplied to and discharged from the blower chamber.

Although the sizes and weights of the sensors and pump, the amounts of sucked gasses, and the capacity of the cells can be reduced by using the above-described microheater and the piezoelectric microblower, it is difficult to achieve a desired result unless the reductions are made in coordination with each other.

For example, even when the size of the sensors and the suction capacity of the pump are reduced, if the capacity of the cells which receive the gasses is too large relative to the size of the sensors and the suction capacity of the pump, the gasses diffuse in the cells and the concentrations thereof decrease. As a result, the desired detection sensitivity cannot be obtained and the response time of the detection operation increases.

Japanese Unexamined Utility Model Registration Application Publication No. 3-60060, for example, describes a detector that is arranged downstream of a column of a GC to detect the components of a sample gas on the basis of thermal conductivities thereof after the components are separated by the column. The detector includes a thin sheet body having a pair of left and right irregular-shaped punch holes. Plate-shaped detector bodies are arranged on either side of the sheet body, and the detector bodies and the sheet body are fastened together with screws. One of the detector bodies has gas inlet holes and gas outlet holes at either side thereof, the gas inlet and outlet holes communicating with the punch holes. Detector attachment holes are formed at intermediate positions between the gas inlet holes and the respective gas outlet holes, and small chip sensors are housed in the attachment holes. The sample gas discharged from the separation column is introduced into one of the gas inlet holes, and carrier gas, which serves as reference gas, is introduced into the other one of the gas inlet holes. The gasses are guided to the respective chip sensors, and the thermal conductivities of the gas components are measured and subjected to comparison to detect the gas components and determine the concentrations thereof. Subsequently, the gasses are discharged through the gas discharge holes.

The above-described detector includes the sheet body in which the pair of irregular-shaped punch holes, which serve as gas passages, are formed at separate positions. The punch holes are provided with the respective gas outlet holes. The detector attachment holes, which have a large diameter, are formed at the intermediate positions of the punch holes. Therefore, it is difficult to form small and uniform punch holes, and the sheet body and the detector bodies have large and complex structures. In addition, since the punch holes have large capacities and dead volumes, diffusion of the introduced gas components occurs. Therefore, the sensing accuracies of the chip sensors are reduced and the desired sensitivity and detection accuracy cannot be obtained.

SUMMARY OF THE INVENTION

An object of the present invention is to solve the above-described problems and provide a gas-leak detector which is suitable for use as, for example, a gas-leak detector for detecting a leakage of carrier gas of a GC; which includes a suction pump and gas detection sensors that are small and integrated together to reduce size and weight of the gas-leak detector and facilitate operation of the gas-leak detector; which has a cell for receiving sucked gasses that has a small capacity so that the gas detection sensors accurately and quickly respond to the gasses and the gas-leak detection sensitivity can be increased; in which pulsation of the suction pump is reduced so that stable detection operation can be achieved; and which can be manufactured at a low cost.

According to an aspect of the present invention, a gas-leak detector includes a suction pump that sucks sample gas that leaks from a test subject and reference gas that serves as a detection reference, two gas detection sensors of a thermal conduction type capable of measuring changes in electric resistances based on thermal conductivities of the respective sucked gasses, and a cell block having a cell therein. The cell is a single space capable of receiving the two sucked gasses. The cell has two suction-gas introduction channels and a single gas discharge channel opening thereinto. The gas-leak detector is capable of detecting a gas leak on the basis of outputs from the two gas detection sensors. The two suction-gas introduction channels and the gas discharge channel open into the cell at a first one of two opposing surfaces of the cell, the opening of the gas discharge channel being arranged between the openings of the two suction-gas introduction channels. The two gas detection sensors are on the same plane as the plane of a second one of the two opposing surfaces of the cell and are arranged between the opening of the gas discharge channel and the openings of the respective suction-gas introduction channels. The suction pump is arranged on the cell block and communicates with the opening of the gas discharge channel. Since the single cell has the two suction-gas introduction channels and the single gas discharge channel, the cell has a simple structure and can be easily manufactured. In addition, the size, capacity, and dead volume of the cell can be reduced, so that diffusion of the sucked gasses in the cell can be suppressed and the detection sensitivity can be increased. Furthermore, since the cell block, in which the gas detection sensors are disposed, and the suction pump are integrated together, the size and weight of the gas-leak detector can be made smaller than those of the gas-leak detector of the related art in which the suction pump and the cells are separately arranged.

In the gas-leak detector, the cell block may have a cut portion and a recessed portion formed therein, the cut portion and the recessed portion communicating with each other, and the cut portion may allow a sensor board to be fitted therein, a sensor chip being connected to the sensor board and housed in the recessed portion so as to define the cell between the sensor chip and the recessed portion. Accordingly, a small cell can be repeatedly and easily manufactured in the assembly process and no special process is required.

In the gas-leak detector, the cell may have a rectangular shape in plan view. Accordingly, the cell can be more easily formed at a lower cost compared to the irregular-shaped cells according to the related art.

In the gas-leak detector, the openings of the two suction-gas introduction channels may be equally spaced from the opening of the gas discharge channel. Accordingly, the cell has a simple structure and can be easily manufactured. In addition, the transportation of the sucked gasses from the suction-gas introduction channels to the gas discharge channel can be repeated and stabilized.

In the gas-leak detector, the two sucked gasses may be transportable from the openings of the respective suction-gas introduction channels toward the respective gas detection sensors and the opening of the gas discharge channel. Accordingly, the two sucked gasses that have merged together are sucked through the gas discharge channel, so that the sucked gasses can be reliably and stably transported.

In the gas-leak detector, the two gas detection sensors may be arranged between the opening of the gas discharge channel and the openings of the respective suction-gas introduction channels so as to be equally spaced from the openings of the respective suction-gas introduction channels. Accordingly, mixing of the two sucked gasses due to the difference in transportation speed therebetween can be suppressed and the gasses can be accurately and stably detected. In addition, the sensing accuracies of the gas detection sensors that detect the transported gasses are stabilized and repeatability thereof is increased, so that the sucked gasses can be accurately detected.

In the gas-leak detector, the openings of the two suction-gas introduction channels, the two gas detection sensors, and the opening of the gas discharge channel may be arranged in the shape of the letter 'V' in plan view. Accordingly, the openings and the sensors can be neatly arranged, so that the cell space can be reasonably utilized and the manufacturing process thereof can be facilitated.

The gas-leak detector may further include a cell sheet having two through holes that communicate with the openings of the respective suction-gas introduction channels, a through hole that communicates with the opening of the gas discharge channel, and a cell passage that communicates with each of the through holes, the cell sheet being airtightly arranged in the cell. Accordingly, the structure of the cell can be streamlined by using the cell sheet, so that the cell can be easily manufactured at a low cost. In addition, the capacity and dead volume of the cell can be reduced, so that diffusion of the sucked gasses in the cell can be suppressed and the detection sensitivity can be increased.

In the gas-leak detector, the two through holes that communicate with the openings of the respective suction-gas introduction channels may be arranged symmetrically with the through hole that communicates with the opening of the gas discharge channel at the center. Accordingly, the cell sheet has a simple structure and can be easily manufactured.

In addition, the transportation of the sucked gasses from the two through holes to the through hole that communicates with the gas discharge channel can be repeated and stabilized.

In the gas-leak detector, the cell passage may be formed in the shape of the letter 'V' in plan view. Accordingly, the size of the cell passage can be reduced and the two holes that communicate with the suction-gas introduction channels and the through hole that communicates with the gas discharge channel can be reasonably arranged neatly along the cell passage.

In the gas-leak detector, the two gas detection sensors may be arranged so as to face the cell passage at positions between the through hole that communicates with the opening of the gas discharge channel and the two through holes that communicate with the openings of the respective suction-gas introduction channels. Accordingly, the gas detection sensors can be arranged on the transportation passages of the sucked gasses that are transported from the suction-gas introduction channels to the gas discharge channel, and the gasses can be reasonably and reliably detected by the gas detection sensors.

In the gas-leak detector, each gas detection sensor may include a microheater. Accordingly, the gas detection sensors can be reduced in size and mass-production thereof can be facilitated to a greater extent than for the gas-leak detector of the related art which includes a filament or a thermister.

In the gas-leak detector, the suction pump may include a micropump driven by a piezoelectric diaphragm capable of vibrating at a high frequency. Accordingly, the suction pump can be reduced in size and the influence of noise caused by pulsation can be reduced. As a result, the operation can be stabilized and the detection sensitivity can be increased.

In the gas-leak detector, a variable current may be applied to each gas detection sensor. Accordingly, the detection sensitivities of the gas detection sensors can be made variable and the gas-leak detector can be used for various types of detections.

DESCRIPTION OF THE PREFERRED EMBODIMENTS

Figure 1:
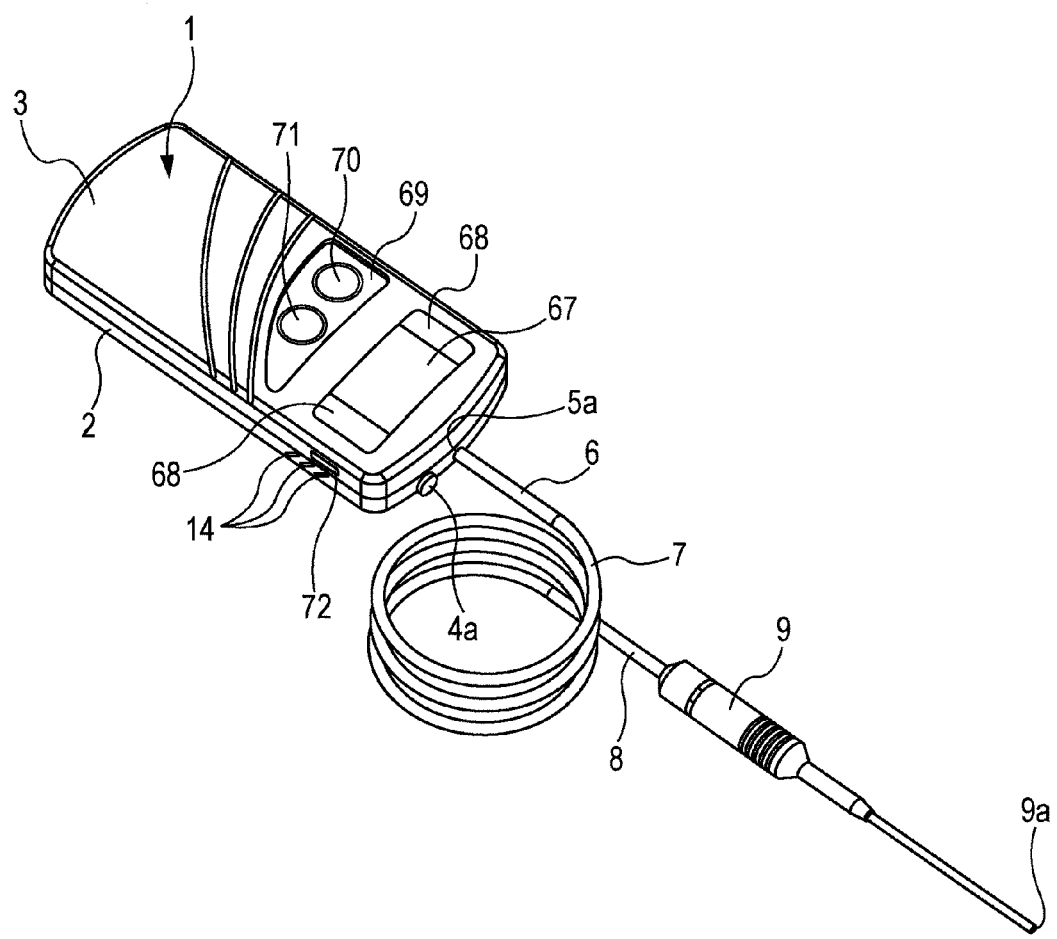
FIG. 1 is a perspective view of a gas-leak detector according to an embodiment of the present invention.

A gas-leak detector according to an embodiment of the present invention illustrated in FIGS. 1 to 8 will now be described. The gas-leak detector is used to detect a carrier gas, which is helium (He) gas in this embodiment, of a GC. Referring to FIGS. 1 to 8, the gas-leak detector includes a portable detector body 1 that substantially has the shape of an oblong rectangular box. The detector body 1 is formed in a box shape by fitting joining portions 2a and 3a of a body casing 2 and a body cover 3, respectively, and fastening them together with screws. The body casing 2 and the body cover 3 are made of a synthetic resin.

In this embodiment, the detector body 1 is 100 mm long, 50 mm wide, and 20 mm thick, and weighs about 105 g. The shape of the detector body 1 is similar to that of a mobile phone.

A suction pipe 4 that allows reference gas, such as air, to be sucked therethrough and an insertion pipe 5 through which a connection pipe, which will be described below, can be inserted are formed integrally with an end part of the joining portion 2a of the body casing 2 at positions close to each other. The suction pipe 4 and the insertion pipe 5 open to the outside at first ends thereof, and air, which serves as the reference gas, can be sucked through a suction hole 4a formed in the suction pipe 4.

A first end of a connection pipe 6 is inserted through an opening 5a of the insertion pipe 5. A second end of the connection pipe 6 projects outward, and the projecting end is connected to a first end of a long suction tube 7. A second end of the suction tube 7 is connected to a connection pipe 8. The connection pipe 8 is connected to a pipe-shaped sample probe 9 with a filter (not shown) interposed therebetween. Sample gas can be sucked through a suction hole 9a at an end of the sample probe 9.

The suction pipe 4 and the insertion pipe 5 project inward from the joining portion 2a at second ends thereof. A filter (not shown) is disposed in the suction pipe 4. The suction pipe 4 has a small diameter portion at the second end thereof, and the small diameter portion is connected to a first end of a communication pipe 10. A second end of the communication pipe 10 is connected to a cell block, which will be described below.

The second end of the connection pipe 6 is inserted through the second end of the insertion pipe 5, and an inwardly projecting end of the connection pipe 6 is connected to a first end of a communication pipe 11. A second end of the communication pipe 11 is connected to the cell block, which will be described below.

The communication pipes 10 and 11 according to this embodiment are tubes made of polytetrafluoroethylene (PTFE) (Teflon (registered trademark)) having an outer diameter of 1.6 mm and an inner diameter of 0.33 mm. The length of the communication pipes 10 and 11 is around 100 mm. Thus, the capacity of the communication pipes 10 and 11 is set to about 8.5 μL to suppress the influence of diffusion of sucked gasses while the gasses are being transported to a cell, which will be described below.

A rectangular plate-shaped battery 12 is placed in a recess (not shown) formed in the bottom surface of the body casing 2. A battery cover 13 is attached to the body casing 2 by being slid along the bottom side of the battery 12, and is fixed to the bottom surface of the body casing 2 with screws.

A plurality of exhaust ports 14 are formed in the joining portion 2a at one side thereof. Gas discharged from a pump, which will be described below, can be discharged to the outside through the exhaust ports 14. A plurality of retaining pins 15 project from the bottom surface of the body casing 2. The retaining pins 15 are engaged with respective cut portions 16 of a board 17 so as to support the board 17.

The board 17 is formed of an oblong rectangular insulating plate on which a wiring pattern (not shown) is printed at a certain position and an electronic circuit is formed. A rectangular liquid crystal display (LCD) device 18 is arranged on the wiring pattern, and certain characters or graphics can be displayed on the LCD device 18.

A plurality of light emitting diodes (LEDs) 19, which are illumination devices arranged on both sides of the LCD device 18, are used as an indicator of the leakage detection when the ambient light is dim that cannot read the LCD, which will be described below.

A large cut portion 20 is formed in the board 17 at the end opposite to the LCD device 18. A cell block 21 is fixed to the bottom surface of the body casing 2 with screws at a position corresponding to the cut portion 20. The cell block 21 is arranged such that the top surface thereof is substantially flush with the top surface of the board 17.

The cell block 21 is substantially box-shaped and is made of an engineering plastic, which is a strong synthetic resin, or polycarbonate. A cut portion 22, which has a rectangular shape in plan view, is formed in the bottom surface of the cell block 21, and a sensor board 23 is housed in the cut portion 22.

The sensor board 23 is formed of a rectangular insulating plate, and has two screw holes 24 at one side thereof. The sensor board 23 is fixed to the cell block 21 by inserting screws 25 through the screw holes 24 from below and screwing the screws 25 into threaded holes, which will be described below, in the cell block 21.

A sensor chip 26 is provided on one side of the sensor board 23 so as to project therefrom. The sensor chip 26 has a smooth and flat top surface, and is housed in a recessed portion 27 which is formed in the top surface of the cut portion 22 and has a rectangular shape in plan view.

A cell 28, which is a small space having a rectangular parallelepiped shape, is formed between the sensor chip 26 and the recessed portion 27. Small amounts of sample gas and reference gas are introduced into the cell 28. The gasses are detected by gas detection sensors, which will be described below, and then transported to a pump, which will be described below.

Figure 5:
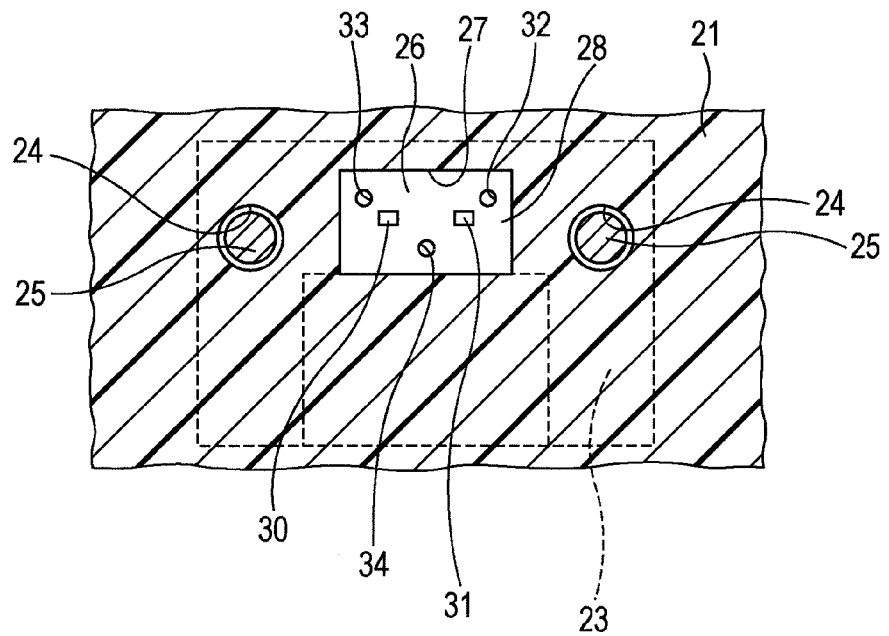
FIG. 5 is an enlarged sectional view of FIG. 4 taken along line V-V.
Figure 6:
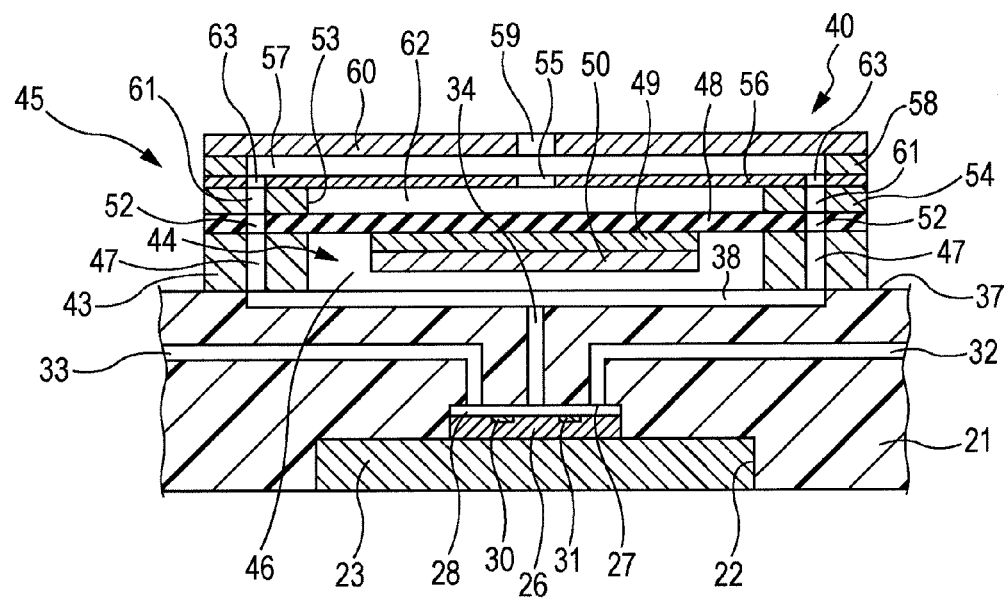
FIG. 6 is a sectional view illustrating the assembly of the cell block and a suction pump according to the embodiment of the present invention in the state before the operation of the suction pump.

The cell 28 of this embodiment can be easily formed by inserting the sensor chip 26 into the recessed portion 27. The cell 28 is a small space having a height in the range of 0.05 to 0.15 mm, and has the same rectangular shape as the shape of the sensor chip 26 in plan view, as illustrated in FIG. 5. The cell capacity of the cell 28 is in the range of 0.05 to 0.5 μL.

The cell capacity of the cell 28 of this embodiment is about 1/600 of the cell capacity according to the related art. The gas suction capacity of the above-described pump is reduced, and the cell capacity is reduced accordingly. The gas suction capacity and the cell capacity are optimized through matching or adjustments, so that the amounts of sucked sample gas and reference gas are reduced and concentrations of the gasses are maintained equivalent so as to suppress diffusion of the gasses in the cell 28 and increase the detection sensitivity.

A constant-current circuit board (not shown), which receives electricity from the battery 12 and controls the operation of the above-described sensors, is provided in the sensor board 23. The constant-current circuit board performs a constant current control, so that electric power consumption can be reduced compared to that of the constant voltage control according to the related art and variation caused by a reduction in the power supply voltage can be prevented.

A connection terminal (not shown) is provided on the sensor board 23 at the other side thereof, and is connected to the constant-current circuit board with lead wires (not shown).

The sensor chip 26 is formed of a rectangular insulating plate, and small gas detection sensors 30 and 31, which include microheaters, are embedded in an intermediate portion of the sensor chip 26 at separate positions. The top surfaces of the gas detection sensors 30 and 31 are flat and flush with the top surface of the sensor chip 26.

In this embodiment, the gas detection sensors 30 and 31 are arranged on a second one of two opposing surfaces of the cell 28, which is a lower surface in this embodiment, at intermediate positions on the lines that connect a gas discharge channel 34 to outlets of gas introduction channels 32 and 33. The gas detection sensors 30 and 31 are arranged symmetrically with the gas discharge channel 34 at the center. This arrangement is illustrated in FIG. 5.

Each of the gas detection sensors 30 and 31 includes a microbridge, which is a small hollow support structure produced by micromachining technology, and a heating portion disposed in the microbridge. The heating portion is caused to respond to the corresponding introduced gas, which is a detection subject, so that an electric property, such as an electric resistance, of the heating portion changes.

The gas detection sensors 30 and 31 are connected to a Wheatstone bridge circuit. When the components of the two gasses around the sensors 30 and 31 change, the thermal conductivities of the gasses change accordingly. This causes temperature changes of the sensors 30 and 31, and the bridge circuit outputs an electric signal representing a change in electric resistances based on the temperature changes. Thus, the amount by which the sample gas is mixed, that is, the amount of leakage can be quantitatively detected.

The current applied to the gas detection sensors 30 and 31 is selectable through the constant-current circuit board. The detection sensitivity of the gas detection sensors 30 and 31 can be selected between a standard sensitivity equivalent to that of the related art and a high sensitivity that is about 20 times as high as that of the related art by changing the current applied to the gas detection sensors 30 and 31.

According to this embodiment, helium gas of 0.01 mL/min at a minimum can be detected at the standard sensitivity, and helium gas of 0.0005 mL/min at a minimum can be detected at the high sensitivity.

The small gas introduction channels 32 and 33 are formed in the cell block 21 so as to extend substantially horizontally. The gas introduction channels 32 and 33 have the outlets that open in a first one of two opposing surfaces of the cell 28, which is an upper surface in this embodiment, at separate positions at either end of the upper surface. Thus, the reference gas sucked through the gas introduction channel 32 and the sample gas sucked through the gas introduction channel 33 can be introduced into the cell 28.

In this embodiment, the opening diameter of the gas introduction channels 32 and 33 is set to 0.33 mm, which is equal to the inner diameter of the communication pipes 10 and 11. The opening diameter is set as small as possible within the range compatible with the suction performance of the suction pump, which will be described below, to achieve the above-described optimization.

Figure 4:
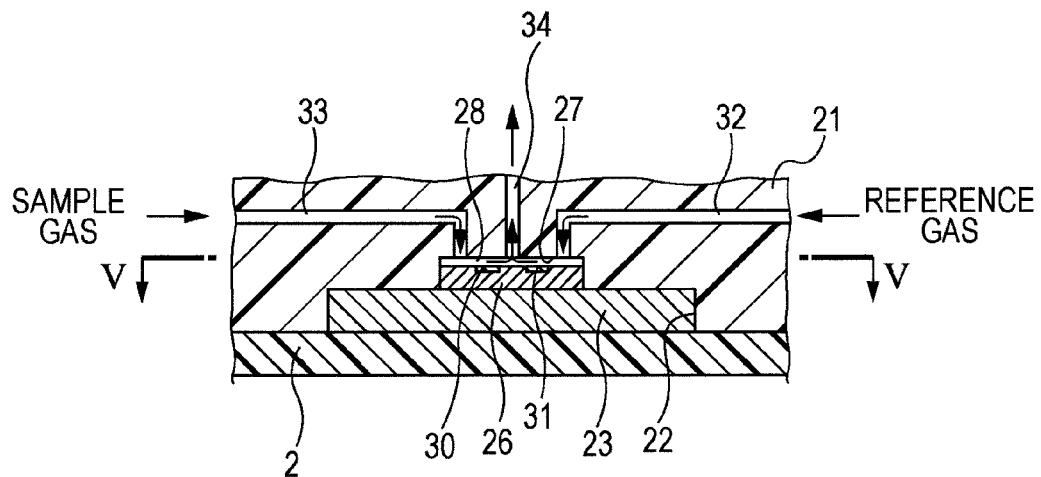
FIG. 4 is an enlarged sectional view of a lower part of the cell block according to the embodiment of the present invention, illustrating the manner in which a sensor board and a sensor chip are assembled in the cell block.

In this embodiment, the gas introduction channels 32 and 33 are arranged on a straight line and on the same plane in the cell block 21 as illustrated in FIGS. 4 and 5. However, the arrangement is not limited to this, and the gas introduction channels 32 and 33 may instead be arranged obliquely or on different planes.

The gas discharge channel 34 is formed in the cell block 21 so as to extend in the thickness direction of the cell block 21. The gas discharge channel 34 has a start end that opens in the first one of the two opposing surfaces of the cell 28 at an intermediate position thereof. A terminal end of the gas discharge channel 34 communicates with the suction pump, which will be described below, at the suction side of the pump so that the gasses introduced into the cell 28 can be discharged to the pump.

FIG. 5 illustrates the arrangement of the outlets of the gas introduction channels 32 and 33 and the start end of the gas discharge channel 34. The outlets of the gas introduction channels 32 and 33 are arranged line symmetrically with the start end of the gas discharge channel 34 at the center. The sensors 30 and 31 are arranged at intermediate positions between the start end of the gas discharge channel 34 and the outlets of the gas introduction channels 32 and 33. The sensors 30 and 31 are arranged line symmetrically with the start end of the gas discharge channel 34 at the center.

The distances from the gas detection sensors 30 and 31 to the outlets of the gas introduction channels 33 and 32, respectively, are set in accordance with the flow rate and transportation speed of the introduced gasses, the detection speed of the sensors 30 and 31, and the suction speed of the gas discharge channel 34 so that the sensors 30 and 31 can reliably detect the introduced gasses.

In this embodiment, the outlets of the gas introduction channels 32 and 33, the start end of the gas discharge channel 34, and the gas detection sensors 30 and 31 are substantially arranged in the shape of the letter 'V' on the cell 28. However, the arrangement is not limited to this. For example, the outlets of the gas introduction channels 32 and 33 and the start end of the gas discharge channel 34 may be arranged on a single straight line, and the sensors 30 and 31 may also be arranged on the same line.

Connection pipes 35 and 36 project from side surfaces of the cell block 21. The connection pipes 35 and 36 are connected to the communication pipes 10 and 11, respectively, at the outer ends thereof, and communicate with the gas introduction channels 32 and 33, respectively, at inner ends thereof.

A substantially rectangular large recess 37 is formed in the top surface of the cell block 21, and a circular hole 38 is formed in the bottom surface of the recess 37. The gas discharge channel 34 opens in the bottom surface of the hole 38 at a central position thereof, and threaded holes (not shown) into which the screws 25 can be screwed are formed on both sides of the opening of the gas discharge channel 34.

A small suction pump 40 that has a low flow rate and can be operated at a high frequency is housed in the recess 37. The pump 40 has the shape of a flat box, and is fixed by inserting screws (not shown) through screw holes (not shown) formed at four corners of the suction pump 40 and screwing the screws into threaded holes (not shown) formed in the bottom surface of the recess 37.

The suction pump 40 of this embodiment is a piezoelectric diaphragm pump in which a diaphragm is vibrated at a high frequency by a piezoelectric element so as to activate a pumping operation of a pump chamber, thereby causing the reference gas and the sample gas to be sucked into and discharged from the suction pump 40. The gas suction capacity of the suction pump 40 is 3.5±0.5 mL/min, which is about one-tenth of that of the suction pump according to the related art.

The piezoelectric diaphragm pump includes a base frame 43, a diaphragm unit 44 supported by the base frame 43, and a pump body 45 arranged on the diaphragm unit 44.

The base frame 43 is formed of a rectangular plate that is larger than the hole 38, and has a large-diameter hollow chamber 46 therein. The hollow chamber 46 is arranged directly above the hole 38 such that the hollow chamber 46 communicates with the hole 38.

A pair of through holes 47 are formed in the base frame 43 so as to communicate with the hole 38.

The diaphragm unit 44 includes a thin diaphragm 48 made of metal, a circular intermediate plate 49 that is bonded to the bottom surface of the diaphragm 48 at a central area thereof, and a disc-shaped piezoelectric element 50 that is bonded to the bottom surface of the intermediate plate 49. The piezoelectric element 50 is made of a piezoelectric ceramic or a lead zirconate titanate (PZT) based material.

The diaphragm 48 is arranged on the base frame 43. The intermediate plate 49 and the piezoelectric element 50 are arranged so as to be capable of being displaced in the hollow chamber 46. The piezoelectric element 50 is connected to a high-frequency driving device (not shown) including an oscillation circuit board. The high-frequency driving device causes the piezoelectric element 50 to expand and contract in the planar direction, thereby causing the diaphragm 48 and the intermediate plate 49, which do not expand or contract, to vibrate at a high frequency in the thickness direction.

A pair of through holes 52 are formed in the diaphragm 48 at the ends thereof so as to communicate with the through holes 47.

The pump body 45 includes a separation plate 54 having a large-diameter through hole 53 therein, a partition plate 56 having a communication hole 55 at the center, a flow-channel plate 58 having a linear flow channel 57 therein, and a cover plate 60 having a discharge hole 59 at the center.

The separation plate 54 is disposed on the diaphragm 48, and a pair of through holes 61, which communicate with the through holes 52, are formed in the separation plate 54 at the ends thereof. The partition plate 56 is disposed on the separation plate 54. The partition plate 56, the diaphragm 48, and the separation plate 54 define the pump chamber 62.

The pump chamber 62 increases and decreases the volume thereof in response to the high-frequency vibration of the diaphragm 48, thereby performing a pumping operation that causes the reference gas and the sample gas to be sucked into the gas introduction channels 32 and 33, respectively, and the introduced gasses to be discharged through the discharge hole 59.

A pair of clearance holes 63, which communicate with the through holes 61, are formed in the partition plate 56 at the ends thereof. The flow channel 57 communicates with the communication hole 55 and the discharge hole 59.

A plurality of threaded holes (not shown) are formed in the top surface of the cell block 21. A pentagonal seal packing member 64 having a hollow inner space therein is disposed on the top surface of the cell block 21, and a pentagonal cell block cover 65 is disposed on the seal packing member 64.

Screw holes (not shown) are formed in each of the seal packing member 64 and the cell block cover 65 at four corners thereof. Screws (not shown) are inserted through the screw holes from the outside of the cell block cover 65, and are screwed into the above-described threaded holes, so that the upper part of the cell block 21 is covered. An exhaust hole 66 is formed at the center of the cell block cover 65 so as to communicate with the discharge hole 59.

The body cover 3 is provided with a transparent, sideways-oriented rectangular display portion 67 at one side thereof.

The display portion 67 is arranged directly above the LCD device 18 so as to make the display of the LCD device 18 visible.

Translucent mask portions 68 that are, for example, black in color, are arranged on both sides of the display portion 67. The mask portions 68 are arranged directly above the LEDs 19 and cover the LEDs 19 in a normal situation to suppress the brightness of the LEDs 19. The LEDs 19 are turned on to be used as an indicator of the leakage levels when the ambient light is dim that cannot read the LCD.

The display portion 67 and the mask portions 68 are formed of a sideways-orientated rectangular synthetic resin plate. The synthetic resin plate is fusion-bonded to the periphery of an opening formed in the body cover 3 at one side thereof such that the surfaces of the synthetic resin plate and the body cover 3 are flush with each other.

A substantially triangular thin sheet-shaped portion (not shown) is provided on the body cover 3 at an intermediate position thereof. A film-shaped seal member 69 is bonded to the surface of the sheet-shaped portion, and two sheet-shaped operation switches 70 and 71 are provided on the seal member 69 in a manner such that the operation switches 70 and 71 can be pressed.

Two contact points (not shown) are arranged directly below the operation switches 70 and 71. The contact points may be electrically connected to the battery 12, the LCD device 18, the LEDs 19, and the constant-current circuit board of the gas detection sensors 30 and 31.

The operation switch 70 is used to turn on and off the battery 12 and set various functions. For example, the operation switch 70 is used to select the detection accuracy from among the high sensitivity and the standard sensitivity, whether to display a leakage mark or a numerical value of concentration on the display portion 67 or LED 19 when a gas leak is detected, and whether to make an alarm buzzer sound if the amount of gas leakage or the concentration is greater than or equal to a certain value.

The operation switch 71 is used to make the display portion 67 display a zero point in a warming-up operation performed before the detection, and is also used as a selection confirmation key in the operation of setting the functions.

Figure 2:
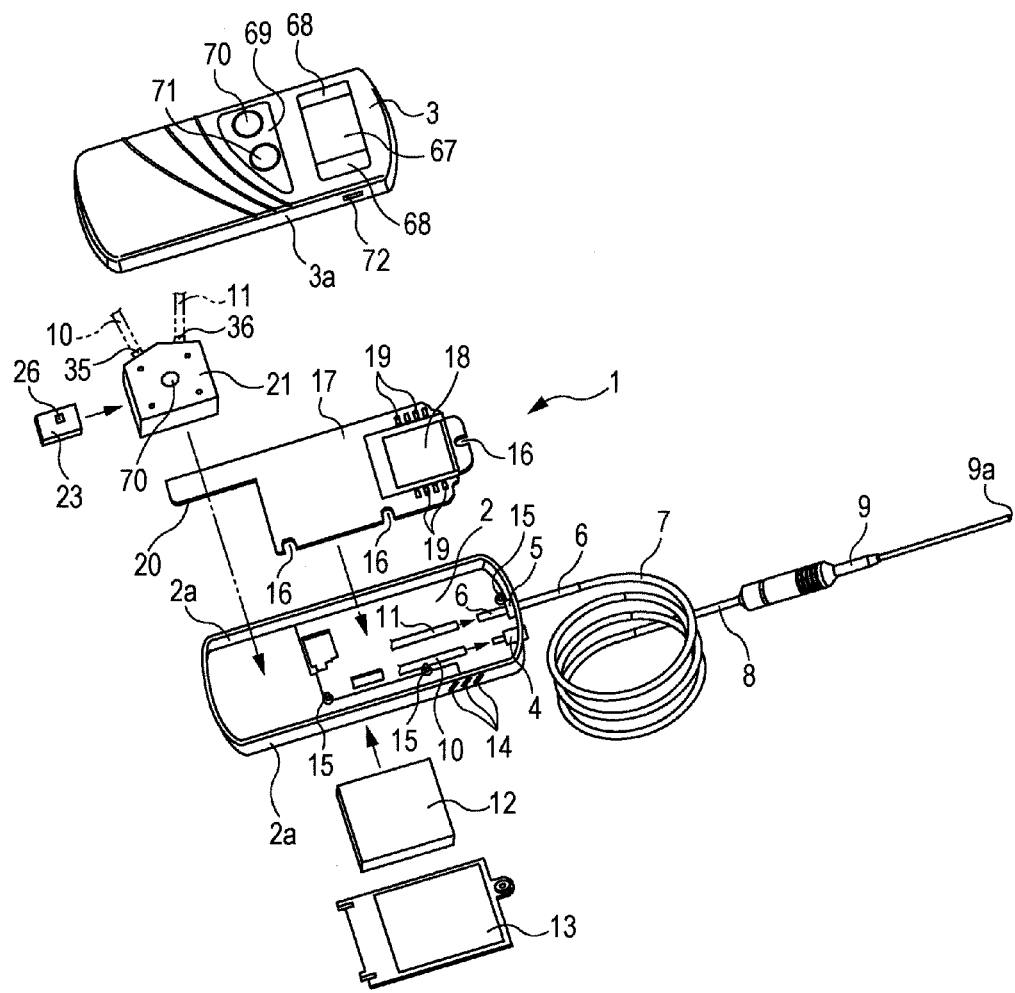
FIG. 2 is an exploded perspective view of the main part of the gas-leak detector according to the embodiment of the present invention.

Referring to FIGS. 1 and 2, a universal serial bus (USB) cable connecting portion 72 provides a connection to a personal computer (not shown) with a USB cable and allows battery charging.

The detector body 1, which is the main part of the gas-leak detector according to the embodiment of the present invention, can be roughly divided into three parts: the body casing 2 and the body cover 3; the board 17 and the cell block 21; and the sensor chip 26 and the suction pump 40.

The body casing 2 is formed substantially in the shape of an oblong rectangular pan by resin molding. The body casing 2 includes the joining portion 2a that projects at the periphery thereof. The suction pipe 4 and the insertion pipe 5 are formed integrally with an upper part of the joining portion 2a. The suction hole 4a and the opening 5a of the suction pipe 4 and the insertion pipe 5, respectively, open to the outside. The exhaust ports 14 are formed in the joining portion 2a at one side thereof.

The body casing 2 has a recess (not shown) in the bottom surface thereof, and the battery cover 13 is attached to the recess with screws.

The body cover 3 is formed substantially in the shape of an oblong rectangular pan that is similar to the shape of the body casing 2 by resin molding. The body cover 3 includes the joining portion 3a that projects at the periphery thereof and that can be fitted to the joining portion 2a. A sideways-oriented rectangular display window is formed in an upper part of the body cover 3. A sideways-oriented rectangular resin plate is fusion-bonded to the periphery of the display window, the resin plate including the transparent display portion 67 and the black mask portions 68 disposed at both sides thereof.

The substantially triangular thin sheet-shaped portion is provided on the body cover 3 at an intermediate position thereof. The seal member 69, on which the two sheet-shaped operation switches 70 and 71 are provided, is bonded to the sheet-shaped portion. The two contact points (not shown) are arranged directly below the operation switches 70 and 71, and are electrically connected to the battery 12, the LCD device 18, the LEDs 19, and the constant-current circuit board of the sensors 30 and 31.

The board 17 is formed of an oblong rectangular insulating plate on which a wiring pattern (not shown) is printed at a certain position. The rectangular LCD device 18 is arranged on the wiring pattern, and the LEDs 19 are arranged on both sides of the LCD device 18. The large cut portion 20 is formed in the board 17 at the end opposite to the LCD device 18.

The cell block 21 is formed substantially in the shape of a box by resin molding, and the cut portion 22 and the recessed portion 27 are formed so as to communicate with each other in the bottom part of the cell block 21. The gas introduction channels 32 and 33 having a small diameter are formed in the cell block 21, and the outlets of the gas introduction channels 32 and 33 open in the top surface of the recessed portion 27 at the ends thereof.

The large recess 37 is formed in the top surface of the cell block 21, and the circular hole 38 is formed in the bottom surface of the recess 37. The gas discharge channel 34, which has the same diameter as that of the gas introduction channels 32 and 33, is formed so as to extend vertically at the center of the hole 38. The threaded holes (not shown) are formed on both sides of the gas discharge channel 34.

One end of the gas discharge channel 34 opens in the top surface of the recessed portion 27 at an intermediate position between the gas introduction channels 32 and 33 at the side opposite to the gas introduction channels 32 and 33. The gas introduction channels 32 and 33 are arranged symmetrically at the top surface of the recessed portion 27 with the gas discharge channel 34 at the center. In this embodiment, the gas introduction channels 32 and 33 and the gas discharge channel 34 are arranged in the shape of the letter 'V' with the gas discharge channel 34 at the center. This arrangement is illustrated in FIG. 5.

The sensor chip 26 is formed of a rectangular insulating plate, and the small gas detection sensors 30 and 31, which include microheaters, are embedded in an intermediate portion of the sensor chip 26 at separate positions. The top surfaces of the gas detection sensors 30 and 31 are flat and flush with the top surface of the sensor chip 26.

In this embodiment, the gas detection sensors 30 and 31 are arranged at intermediate positions on the lines that connect the gas discharge channel 34 to the gas introduction channels 32 and 33, and are arranged symmetrically with the gas discharge channel 34 at the center.

Each of the gas detection sensors 30 and 31 includes a microbridge, which is a small hollow support structure, and a heating portion disposed in the microbridge. The heating portion is caused to respond to the corresponding introduced gas, which is a detection subject, so that an electric property, such as an electric resistance, of the heating portion changes.

The gas detection sensors 30 and 31 are connected to a Wheatstone bridge circuit. The bridge circuit outputs an electric signal representing a change in electric resistances based on changes in the components of the two introduced gasses around the sensors 30 and 31, in other words, temperature changes of the sensors 30 and 31 caused by changes in the thermal conductivities of the gasses. Thus, the amount by which the sample gas is mixed, that is, the amount of leakage can be quantitatively detected.

In this embodiment, the current applied to the gas detection sensors 30 and 31 is selectable through the constant-current circuit board. The detection sensitivity of the gas detection sensors 30 and 31 can be selected between the standard sensitivity and the high sensitivity by changing the current applied to the gas detection sensors 30 and 31.

The suction pump 40 is a piezoelectric diaphragm pump including the base frame 43, the diaphragm unit 44, and the pump body 45.

The diaphragm 48, the separation plate 54, the partition plate 56, the flow-channel plate 58, and the cover plate 60 are stacked in that order on the base frame 43, so that the through holes 47, 52, and 61, the clearance hole 63, the flow channel 57, and the discharge hole 59 formed in these elements communicate with each other.

The diaphragm 48, the separation plate 54, and the partition plate 56 define the pump chamber 62. The piezoelectric element 50 is bonded to the bottom surface of the diaphragm 48 with the intermediate plate 49 interposed therebetween, and is connected to the high-frequency driving device (not shown).

In the assembly process of the gas-leak detector including the main components that are produced in the above-described manner, the sensor chip 26 is bonded to one side of the sensor board 23, in which the constant-current circuit board (not shown) is embedded, to form a sensor chip assembly. The sensor chip assembly is inserted into the cut portion 22 in the lower part of the cell block 21 so that the sensor chip 26 is inserted into the recessed portion 27.

Subsequently, the screws 25 are inserted through the screw holes 24, and are screwed into the threaded holes (not shown) formed in the upper part of the cell block 21. Thus, the assembly is fixed to the lower part of the cell block 21.

Figure 3:
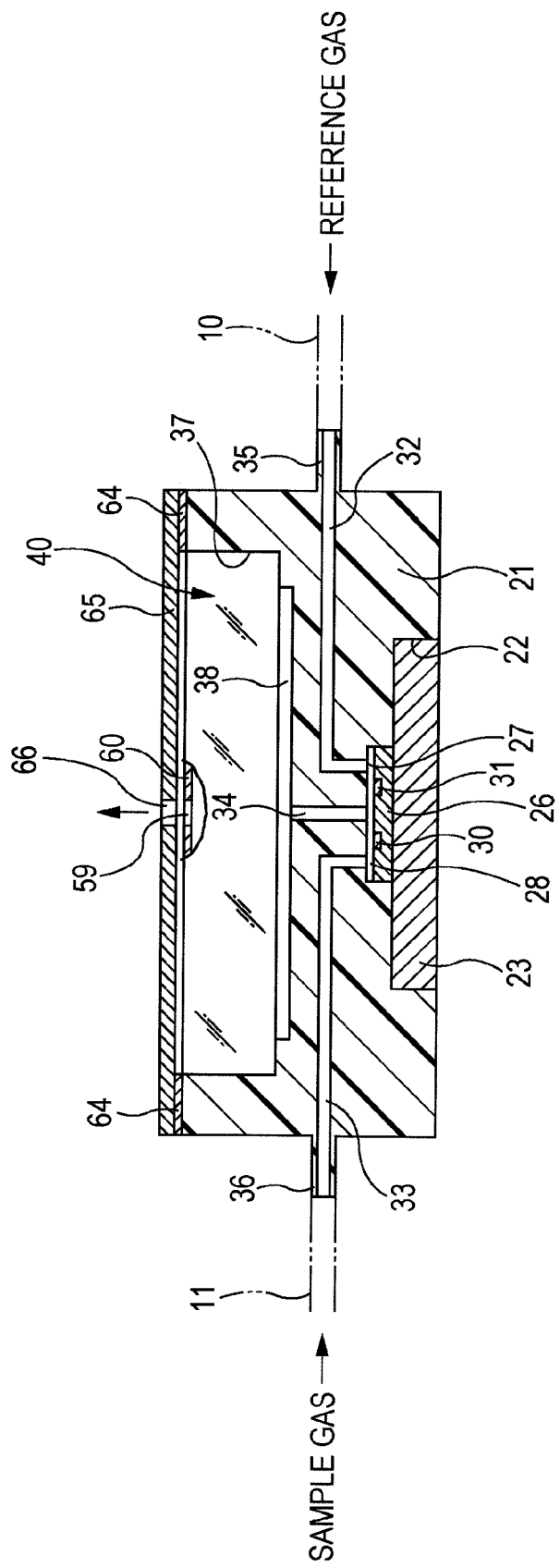
FIG. 3 is a sectional view of a cell block according to the embodiment of the present invention.

FIGS. 3 to 5 illustrate the manner in which the sensor chip assembly is attached to the cell block 21. The sensor board 23 and the sensor chip 26 are fitted to the cut portion 22 and the recessed portion 27, respectively, so that the cell 28, which is a single small space having a rectangular parallelepiped shape, is formed between the top surface of the sensor chip 26 and the top surface of the recessed portion 27. The gas detection sensors 30 and 31 are arranged so as to face the cell space.

As described above, according to the embodiment of the present invention, the cell 28 is formed as a result of the cell block 21, the sensor board 23, and the sensor chip 26 being assembled together. It is not necessary to manufacture a sheet body having a complex structure as in the related art or subject the top surface of the recessed portion 27 to a complex molding or machining process.

More specifically, unlike the structure of the related art in which the irregular-shaped cells are formed at separate positions, the cell 28 is a single space having the same shape as that of the sensor chip 26. The cell 28 has a simple structure and can be easily manufactured.

The gas introduction channels 32 and 33 open in the top surface of the recessed portion 27 that faces the cell 28, that is, in the first one of two opposing surfaces of the cell 28, which is the upper surface of the cell 28. The suction hole at the start end of the gas discharge channel 34 is formed between the openings of the gas introduction channels 32 and 33. In an example of the related art, gas inlet and outlet holes are formed for each of two cells in a detector body that faces the cells, and large-diameter sensor attachment holes are formed between the gas inlet and outlet holes. This requires complex processing. In contrast, in this embodiment, the capacity and dead volume of the cell 28 are reduced, and the cell 28 can be manufactured easily and uniformly.

In this embodiment, the gas introduction channels 32 and 33 open into the cell 28 at the first one of the two opposing surfaces of the cell 28, and the gas detection sensors 30 and 31 are arranged on the second one of the two opposing surfaces. However, the gas introduction channels 32 and 33 and the gas detection sensors 30 and 31 may instead be arranged at the opposite surfaces. Alternatively, the opposing surfaces of the cell 28 may be side surfaces that oppose each other instead of the upper and lower surfaces.

In this embodiment, as illustrated in FIG. 5, the outlets of the gas introduction channels 32 and 33 and the start end of the gas discharge channel 34 are arranged in the shape of the letter 'V' in plan view on the top surface of the recessed portion 27, and the outlets of the gas introduction channels 32 and 33 are arranged symmetrically with the start end of the gas discharge channel 34 at the center. Thus, the structure is simplified and the manufacturing process is facilitated. The distance from each of the gas introduction channels 32 and 33 to the gas discharge channel 34 is reasonably set so that the gasses are not mixed while being transported to and detected by the sensors 30 and 31.

The gas detection sensors 30 and 31 are arranged at intermediate positions between the start end of the gas discharge channel 34 and the outlets of the gas introduction channels 32 and 33 such that the surfaces of the sensors 30 and 31 are flush with the top surface of the sensor chip 26. The sensors 30 and 31 are arranged symmetrically with the start end of the gas discharge channel 34 at the center.

The suction pump 40 is housed in the recess 37 in the upper part of the cell block 21, and is fixed by inserting screws (not shown) through screw holes (not shown) formed at four corners of the suction pump 40 and screwing the screws into threaded holes (not shown) formed in the recess 37.

After the suction pump 40 is fixed, the seal packing member 64 is placed on the top end surface of the cell block 21, and the cover plate 65 is placed on the packing member 64. Screws (not shown) are inserted through screw holes (not shown) formed in the packing member 64 and the cover plate 65 and are screwed into threaded holes formed in the cell block 21, so that the top end surface of the cell block 21 is covered.

The suction pump 40 is assembled in the cell block 21 in the above-described manner, and the cell block 21 is installed in the lower part of the body casing 2. After that, the suction pipe 4 in the body casing 2 is connected to the first end of the communication pipe 10 with a filter (not shown) interposed therebetween, and the inner end of the insertion pipe 5 is connected to the first end of the communication pipe 11. The second ends of the communication pipes 10 and 11 are connected to the connection pipes 35 and 36, respectively.

Next, the board 17 is installed in the body casing 2 in a supported state by engaging the cut portions 16 with the retaining pins 15, and the body cover 3 to which the seal member 69 is bonded is attached to the body casing 2. The joining portions 3a and 2a of the body cover 3 and the body casing 2 are fitted to each other, and then fastened together with screws.

Subsequently, the first end of the connection pipe 6 is inserted into the insertion pipe 5 such that the second end projects outward, and the first end of the long suction tube 7 is connected to the projecting end of the connection pipe 6. The connection pipe 8 is connected to the second end of the suction tube 7, and the sample probe 9 is connected to the connection pipe 8 with a filter (not shown) interposed therebetween. This completes the assembly process.

As described above, in the gas-leak detector according to the embodiment of the present invention, each of the gas detection sensors 30 and 31 includes a microheater provided with a microbridge instead of a platinum coil, a thermister, or a filament included in the gas-leak detector of the related art. The sensors 30 and 31 are reduced in size and mass production thereof is realized, so that the cost of the sensors 30 and 31 can be reduced. The sensor board 23 and the sensor chip 26 on which the sensors 30 and 31 are mounted are also reduced in size.

In addition, the suction pump 40 is a piezoelectric driven diaphragm pump instead of a direct-current motor driven diaphragm pump used as a suction pump in the related art. Accordingly, the size and weight of the pump 40 are reduced. Since the pump 40 is housed in the cell block 21, the size and weight of the cell block 21 are also reduced.

Furthermore, the gas detection sensors 30 and 31 and the sensor board 23 are housed in the lower part of the cell block 21 and the suction pump 40 is housed in the upper part of the cell block 21 such that they are arranged integrally in the vicinity of each other. As a result, the size and weight of the gas-leak detector can be made smaller than those of the gas-leak detector of the related art in which the sensors and the pump are separately arranged.

In this embodiment, the detector body 1 substantially has the shape of a 100 mm long, 50 mm wide, and 20 mm thick mobile phone. The volume of the detector body 1 is about one third or less of that of the detector body of the related art. The weight of the detector body 1 is about 95 g, which is about one thirds of that of the detector body of the related art. Thus, the detector body 1 is small and light, which makes it easier to store when not in use and carry and handle when in use.

When a gas leak test is performed using the gas-leak detector that is assembled in the above-described manner, a warming-up operation is performed before the test. More specifically, the operation switch 70 is turned on, so that a high frequency pulse voltage is applied to the piezoelectric element 50. Accordingly, the diaphragm 48 vibrates in the thickness direction at a high frequency, thereby causing the pump chamber 62 to perform a pumping operation. Thus, the suction pump 40 is driven and positive and negative pressures are alternately produced in the flow channel 57 and the hollow chamber 46, which communicate with the pump chamber 62.

When the diaphragm 48 is moved so as to curve downward, the volume of the pump chamber 62 increases and a negative pressure is produced, so that the introduced gas in the flow channel 57 flows into the pump chamber 62 through the communication hole 55.

Figure 7:
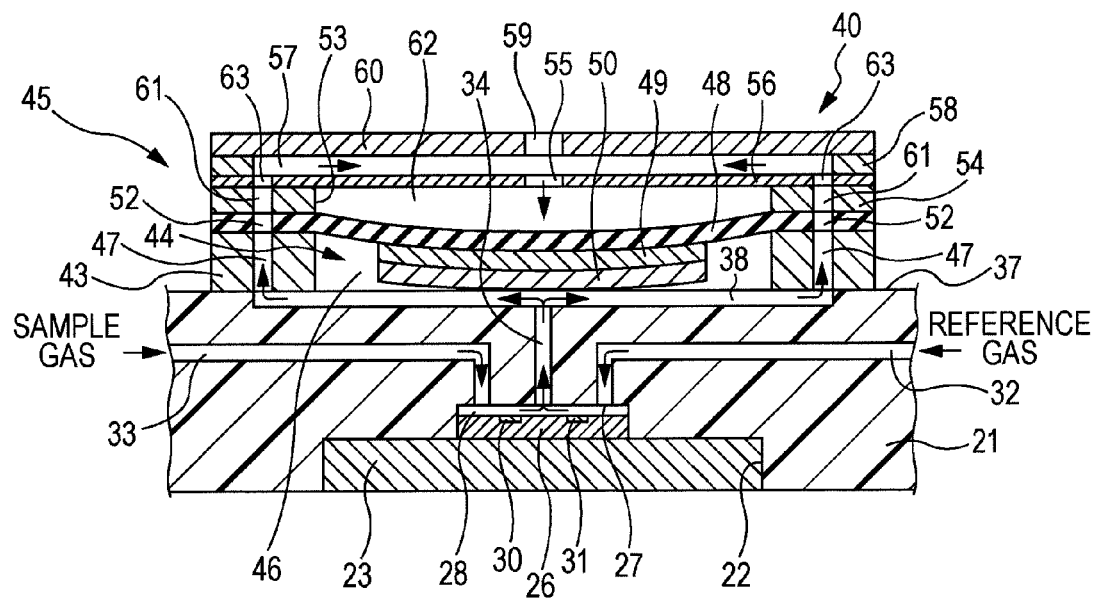
FIG. 7 is a sectional view illustrating the operational state of the suction pump according to the embodiment of the present invention in which a diaphragm is downwardly curved.

Owing to the movement of the diaphragm 48, the introduced gas in the hollow chamber 46 is pushed toward the flow channel 57, and the introduced gas in the hole 38 is drawn in the same direction in response to the above-described gas flow, which induces the transportation of the introduced gas. This state is illustrated in FIG. 7.

In response to the transportation of the introduced gas in the hole 38, the introduced gas in the gas discharge channel 34 is sucked so as to induce the gas suction from the gas introduction channels 32 and 33 through the cell 28. Accordingly, the reference gas is sucked through the connection pipe 10 from the suction pipe 4, and the sample gas is sucked through the connection pipe 11 from the sample probe 9.

When the diaphragm 48 is moved so as to curve upward, the volume of the pump chamber 62 decreases and a positive pressure is produced, so that the introduced gas in the pump chamber 62 is forced out to the flow channel 57 through the communication hole 55. The introduced gas is discharged through the discharge hole 59 to the inner space of the detector body 1, and is discharged to the outside through the exhaust ports 14.

When the introduced gas flows out through the discharge hole 59, the introduced gas in the flow channel 57 is drawn by the gas flow and flows toward the center of the flow channel 57. This induces the transportation of the introduced gas in the hollow chamber 46 and the hole 38, which communicate with the flow channel 57.

Figure 8:
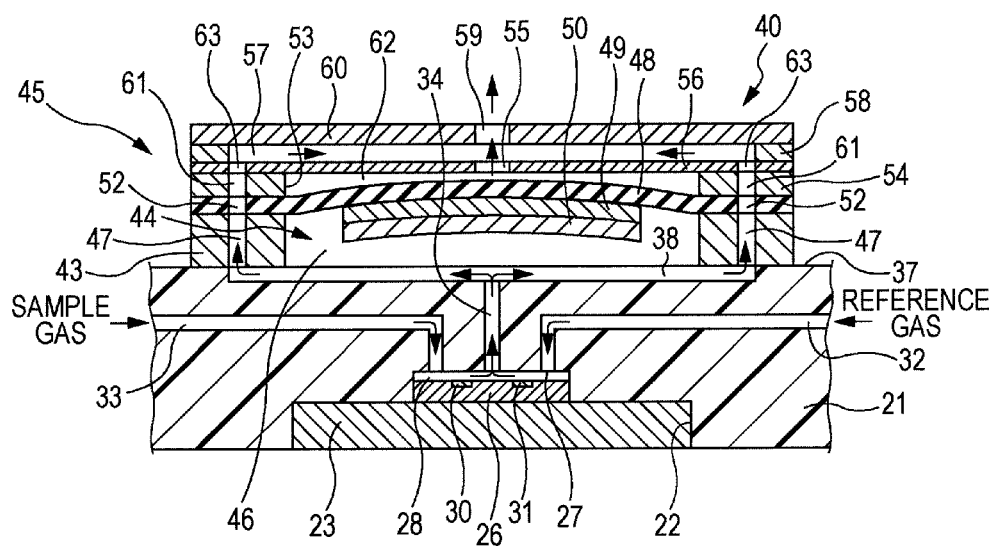
FIG. 8 is a sectional view illustrating the operational state of the suction pump according to the embodiment of the present invention in which the diaphragm is upwardly curved.
Figure 9:
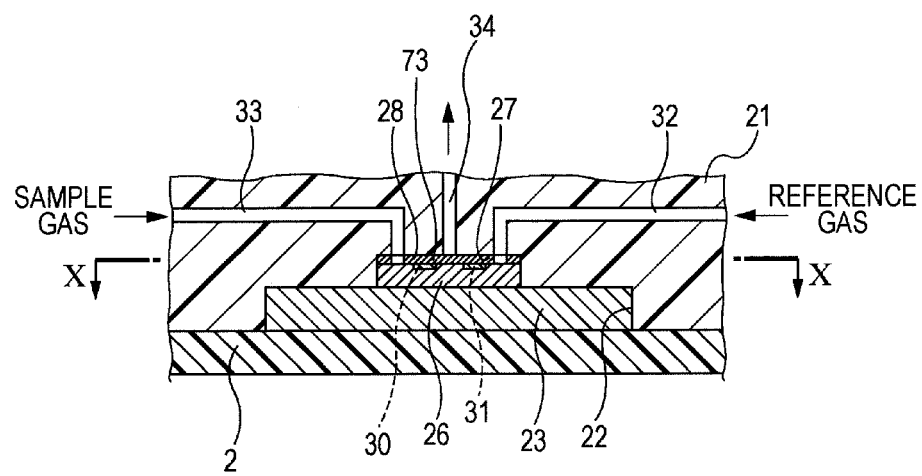
FIG. 9 is a sectional view of the main part of a gas-leak detector according to another embodiment of the present invention.

In addition, owing to the movement of the diaphragm 48, the volume of the hollow chamber 46 increases and a negative pressure is produced, so that the introduced gas in the gas discharge channel 34, which communicates with the hollow chamber 46, is sucked so as to induce the gas suction from the gas introduction channels 32 and 33 through the cell 28. Accordingly, the reference gas is sucked through the connection pipe 10 from the suction pipe 4, and the sample gas is sucked through the connection pipe 11 from the sample probe 9. This state is illustrated in FIG. 8.

When the operation switch 70 is turned on, a current corresponding to the detection sensitivity is applied to the gas detection sensors 30 and 31 by the constant-current circuit board (not shown). Accordingly, the sensors 30 and 31 generate heat and start the detecting operation.

The temperatures of the gas detection sensors 30 and 31 change in accordance with changes in the thermal conductivities of the introduced gasses that are being transported. The bridge circuit to which the sensors 30 and 31 are connected outputs an electric signal representing the changes in the electric resistances based on the temperature changes.

In the above-described warming-up operation, the sensors 30 and 31 receive the same gas, so that the components and thermal conductivities of the introduced gasses do not change. Therefore, the bridges are in a state of equilibrium. After the warming-up operation, the display portion 67 shows a zero indication that represents the state in which mixing of gas having different components does not occur, that is, the state in which gas leak is not detected. If the display portion 67 shows an indication of gas leak after the warming-up operation, the operation switch 71 is operated to correct the zero point for the display of a gas leak.

After the normal operation of the gas-leak detector is confirmed or the adjustment is performed after the warming-up operation, an actual operation of detecting a leakage of carrier gas of a GC may be performed in the following manner. That is, while the GC is performing an analytical operation with the carrier gas being supplied, an operator holds the gas-leak detector and moves the suction hole 9a of the sample probe 9 to locations to be tested, such as a pipeline of the carrier gas, a sample introduction portion, and a separation column of the GC, and causes the sample probe 9 to suck the surrounding gas as the sample gas.

While the sample gas is being sucked, the air at a location separated from the locations to be tested is also sucked through the suction hole 4a of the suction pipe 4 as the reference gas.

The sucked sample gas and reference gas are guided to the cell 28 through the communication pipes 10 and 11 and the gas introduction channels 32 and 33 as described above. The gasses are transported from the outlets of the gas introduction channels 32 and 33 and over the gas detection sensors 30 and 31, sucked into the gas discharge channel 34, and transported toward the hollow chamber 46.

The gas discharge channel 34 is equally spaced from the outlets of the sample gas and the reference gas, and the gas detection sensors 30 and 31 are arranged between the gas discharge channel 34 and the outlets at positions equally spaced from the outlets. Therefore, the introduced gasses are transported over the sensors 30 and 31 without merging with each other, and the temperature changes of the sensors 30 and 31 are caused purely by the respective introduced gasses. As a result, a precise and stable electric signal is output and the reliability of the detection accuracy is increased.

If the helium gas, which is the carrier gas, is mixed in the sample gas, the components of the gas change. As a result, the thermal conductivity of the gas changes, thereby causing a change in the temperatures of the gas detection sensors 30 and 31.

The bridge circuit outputs an electric signal representing a change in electric resistances based on the temperature changes. Thus, the amount of leak gas that has been mixed can be quantitatively detected, and is displayed on the display portion 67. If the amount or concentration of the leak gas is greater than or equal to a certain value, an alarm buzzer is caused to sound.

In the embodiment of the present invention, the concentration of the sample gas is increased by reducing the suction capacity of the suction pump 40 for sucking the sample gas and the reference gas to about one-tenth of that of the suction pump according to the related art. In addition, the operation of the suction pump 40 is stabilized by driving the piezoelectric element 50 at a high frequency and reducing the influence of pulsation. Thus, the sensitivity and stability of the detecting operation are increased.

The inner diameters of the sample probe 9, the suction tube 7, the connection pipe 6, the communication pipes 10 and 11, and the gas introduction channels 32 and 33, which form introduction passages for the gasses that are sucked and introduced to the cell 28, are reduced in accordance with the suction capacity of the suction pump 40. Thus, the internal volumes of the introduction passages are reduced, so that diffusion of the introduced gasses during transportation thereof and response delay can be reduced. Thus, the sensitivity and stability of the detecting operation are increased.

The volume of the cell 28, that is, the cell capacity, is set so as to match the shape and response characteristics of the gas detection sensors 30 and 31. The amounts of sample gas and reference gas are both reduced to about 1/600 of the amounts of the gases according to the related art, so that the influence of diffusion in the cell 28 is reduced. Accordingly, the concentration of leak gas is not reduced and the desired sensitivity can be achieved. Furthermore, the response time required to detect the gas leak is reduced.

As described above, according to the embodiment of the present invention, the small suction capacity of the suction pump 40, the gas introduction passages suitable for the suction capacity, and the cell capacity are reasonably adjusted and optimized. As a result, a small, light, high-sensitivity gas-leak detector having stable detection characteristics is provided.

In this embodiment, a detectable amount of leakage of helium gas is about 1/20 of the detectable amount according to the related art. Thus, a high detection sensitivity is achieved.

FIGS. 9 to 12 illustrate another embodiment of the present invention. Components similar to those in the above-described structure are denoted by the same reference numerals.

In the above-described embodiment, the cell 28 is formed between the sensor chip 26 and the recessed portion 27, and the flow channels from the outlets of the introduced gasses to the gas discharge channel 34 are flexible in the cell 28. In contrast, in this embodiment, a cell sheet 73, which has the same shape and thickness as those of the cell 28, is airtightly arranged in the cell 28.

The cell sheet 73 is formed of a synthetic resin plate having a rectangular or rectangular parallelepiped shape that is the same as the shape of the cell 28. The cell sheet 73 has a plurality of through holes 74 to 76 at positions corresponding to the outlets of the gas introduction channels 32 and 33 and the start end of the gas discharge channel 34.

Figure 10:
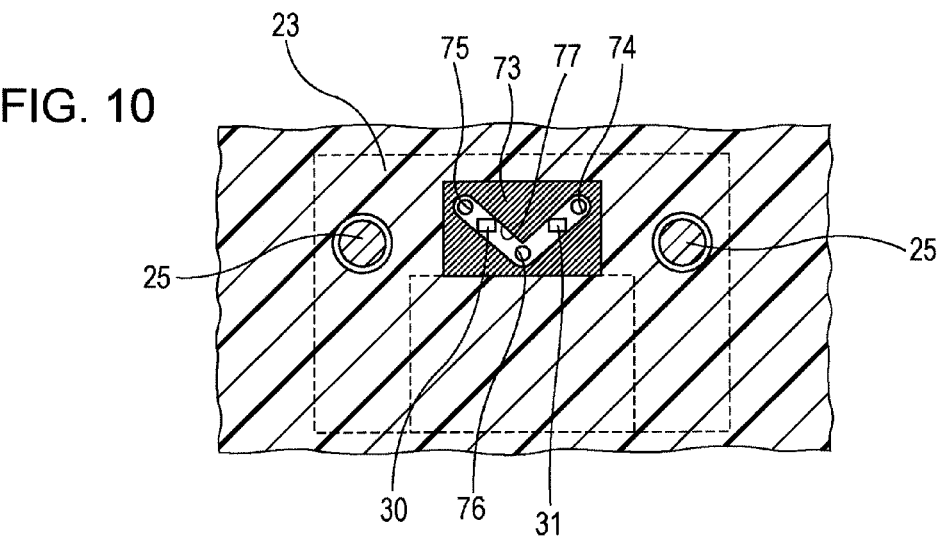
FIG. 10 is a sectional view of FIG. 9 taken along line X-X.
Figure 11:
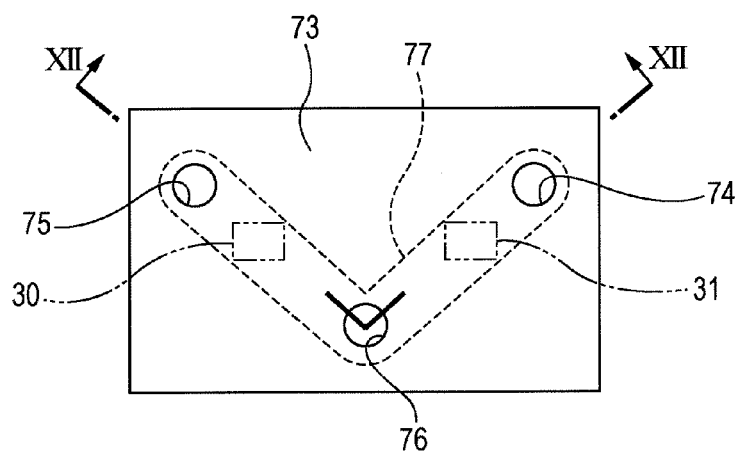
FIG. 11 is an enlarged plan view of a cell sheet included in the gas-leak detector illustrated in FIG. 9.
Figure 12:
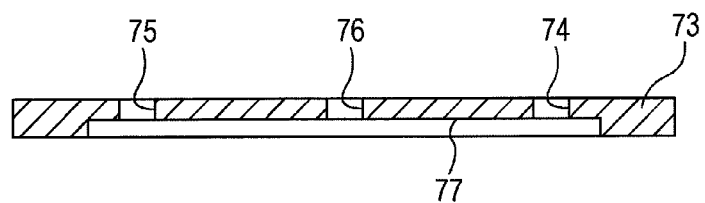
FIG. 12 is an enlarged sectional view of FIG. 11 taken along line XII-XII.

As illustrated in FIGS. 10 and 11, the through holes 74 to 76 are arranged substantially in the shape of the letter 'V' in the cell sheet 73, and the through holes 74 and 75 are arranged symmetrically with the through hole 76 at the center. A cell passage 77 that substantially has the shape of the letter 'V' is formed so as to extend through the through holes 74 and 76 in plan view.

The cell passage 77 is formed in the bottom surface of the cell sheet 73, and the through holes 74 to 76 open in the top surface of the cell passage 77. The gas detection sensors 30 and 31 are arranged directly below the cell passage 77.

The gas detection sensors 30 and 31 are respectively arranged at intermediate positions between the through holes 75 and 76 and between the through holes 76 and 74, and are arranged symmetrically with the through hole 76 at the center.

The through holes 74 and 76 and the cell passage 77 may be easily and uniformly formed when the cell sheet 73 is formed by resin-molding. Therefore, compared to the case in which, for example, the through holes 74 to 76 and the cell passage 77 are formed in an upper part of the sensor chip 26, the manufacturing process can be facilitated and the cost can be reduced.

In addition, unlike the cell 28 of the above-described embodiment, only the cell passage 77, whose capacity corresponds to the cell capacity, is used as the gas channel so that the capacity of the gas channel is reduced. Therefore, diffusion and reduction in concentration of the introduced gasses in the cell passage 77 are suppressed, and high-sensitivity detection can be achieved.

The cell passage 77 regulates the flow of the introduced gasses so that the introduced gasses are directly and quickly transported to the gas detection sensors 30 and 31. Therefore, the sensors 30 and 31 precisely respond to the introduced gasses and perform an accurate detection with high stability.

Therefore, compared to the sheet body according to the related art which is produced by forming the irregular-shaped cells in a plate at separate positions, the structure is simplified and the manufacturing process is facilitated. In addition, since the cell passage 77 is formed so as to take up substantially one-half or less of the cell sheet 73 in the thickness direction, the cell capacity and the dead volume can be reduced. As a result, diffusion of the gas components can be suppressed and the detection sensitivity can be increased.

When the cell sheet 73 is used, the cell sheet 73 is airtightly installed by pressing the cell sheet 73 against the upper part of the recessed portion 27. The through holes 74 and 76 are placed at positions corresponding to the outlets of the gas introduction channels 32 and 33 and the start end of the gas discharge channel 34, and the cell passage 77 is arranged directly above the gas detection sensors 30 and 31.

When the sample gas and the reference gas are introduced into the cell block 21 in which the cell sheet 73 is installed, the gasses flow into the cell passage 77 through the through holes 75 and 74, and are quickly transported over the gas detection sensors 30 and 31 by being guided by the cell passage 77. The sensors 30 and 31 respond to the gasses, and reliably and accurately detect the changes in the components and thermal conductivities of the gasses. Thus, a gas leak can be quickly detected with high sensitivity.

A gas-leak detector according to an embodiment of the present invention includes a suction pump and gas detection sensors that are small and integrated together to reduce the size and weight of the gas-leak detector and facilitate operation of the gas-leak detector, and has a cell for receiving sucked gasses that has a small capacity so that the gas detection sensors accurately and quickly respond to the gasses and the gas-leak detection sensitivity can be increased. Pulsation of the suction pump is reduced so that stable detection operation can be achieved, and the gas-leak detector can be manufactured at a low cost. The gas-leak detector is therefore suitable for use as, for example, a gas-leak detector for detecting a leakage of carrier gas of a gas chromatograph.

What is claimed is:

1. A gas-leak detector comprising:
   a suction pump that sucks sample gas that leaks from a test subject and reference gas that serves as a detection reference;
   two gas detection sensors capable of measuring changes in electric resistances based on thermal conductivities of the respective sucked gasses; and
   a cell block having a cell therein, the cell being a single space capable of receiving the two sucked gasses, the cell having two suction-gas introduction channels and a single gas discharge channel opening thereinto,
   wherein the gas-leak detector is capable of detecting a gas leak on the basis of outputs from the two gas detection sensors,
   wherein the two suction-gas introduction channels and the gas discharge channel open into the cell at a first one of two opposing surfaces of the cell, the opening of the gas discharge channel being arranged between the openings of the two suction-gas introduction channels,
   wherein the two gas detection sensors and a second one of the two opposing surfaces of the cell are on a same plane and the two gas detection sensors are arranged between the opening of the gas discharge channel and the openings of the respective suction-gas introduction channels, and
   wherein the suction pump is arranged on the cell block and communicates with the opening of the gas discharge channel.

2. The gas-leak detector according to claim 1, further comprising:
   a cut portion and a recessed portion formed in the cell block, the cut portion and the recessed portion communicating with each other,
   a sensor board fitted in the cut portion, and
   a sensor chip connected to the sensor board and housed in the recessed portion so as to define the cell between the sensor chip and the recessed portion.

3. The gas-leak detector according to claim 1, wherein the cell has a rectangular shape in plan view.

4. The gas-leak detector according to claim 1, wherein the openings of the two suction-gas introduction channels are equally spaced from the opening of the gas discharge channel.

5. The gas-leak detector according to claim 4, wherein the two gas detection sensors are arranged between the opening of the gas discharge channel and the openings of the respective suction-gas introduction channels so as to be equally spaced from the openings of the respective suction-gas introduction channels.

6. The gas-leak detector according to claim 1, wherein the two sucked gasses are transportable from the openings of the respective suction-gas introduction channels toward the respective gas detection sensors and the opening of the gas discharge channel.

7. The gas-leak detector according to claim 1, wherein the openings of the two suction-gas introduction channels, the two gas detection sensors, and the opening of the gas discharge channel are arranged in the shape of the letter 'V' in plan view.

8. The gas-leak detector according to claim 1, further comprising:
   a cell sheet having two through holes that communicate with the openings of the respective suction-gas introduction channels, a through hole that communicates with the opening of the gas discharge channel, and a cell passage that communicates with each of the through holes, the cell sheet being airtightly arranged in the cell.

9. The gas-leak detector according to claim 8, wherein the two through holes that communicate with the openings of the respective suction-gas introduction channels are arranged symmetrically with the through hole that communicates with the opening of the gas discharge channel at the center.

10. The gas-leak detector according to claim 8, wherein the cell passage is formed in the shape of the letter 'V' in plan view.

11. The gas-leak detector according to claim 8, wherein the two gas detection sensors are arranged so as to face the cell passage at positions between the through hole that communicates with the opening of the gas discharge channel and the two through holes that communicate with the openings of the respective suction-gas introduction channels.

12. The gas-leak detector according to claim 1, wherein each gas detection sensor includes a microheater.

13. The gas-leak detector according to claim 1, wherein the suction pump includes a micropump driven by a piezoelectric diaphragm capable of vibrating at a high frequency.

14. The gas-leak detector according to claim 1, wherein a variable current is applied to each gas detection sensor.

* * * * *